(12) United States Patent
Lalleman et al.

(10) Patent No.: US 8,808,401 B2
(45) Date of Patent: Aug. 19, 2014

(54) HAIR DYEING PROCESS USING AN INSOLUBLE SILICATE, AN AROMATIC COMPOUND AND A HYDROXYLATED ALIPHATIC SOLVENT

(75) Inventors: Boris Lalleman, Paris (FR); Françoise Albouy, Rueil Malmaison (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/995,647

(22) PCT Filed: Dec. 19, 2011

(86) PCT No.: PCT/EP2011/073231
§ 371 (c)(1),
(2), (4) Date: Jun. 19, 2013

(87) PCT Pub. No.: WO2012/084818
PCT Pub. Date: Jun. 28, 2012

(65) Prior Publication Data
US 2013/0263389 A1     Oct. 10, 2013

Related U.S. Application Data

(60) Provisional application No. 61/434,076, filed on Jan. 19, 2011, provisional application No. 61/434,530, filed on Jan. 20, 2011, provisional application No. 61/434,531, filed on Jan. 20, 2011.

(30) Foreign Application Priority Data

Dec. 20, 2010 (FR) .................................... 10 60798
Dec. 20, 2010 (FR) .................................... 10 60800
Dec. 20, 2010 (FR) .................................... 10 60803

(51) Int. Cl.
*A61Q 5/10* (2006.01)

(52) U.S. Cl.
USPC ............... 8/405; 8/406; 8/408; 8/435; 8/426; 8/632; 8/646; 132/202; 132/208

(58) Field of Classification Search
USPC ............. 8/405, 406, 408, 435, 426, 632, 646, 8/202, 208
See application file for complete search history.

(56) References Cited

U.S. PATENT DOCUMENTS

| | | |
|---|---|---|
| 3,869,454 A | 3/1975 | Lang et al. |
| 3,955,918 A | 5/1976 | Lang |
| 3,985,499 A | 10/1976 | Lang et al. |
| 4,003,699 A | 1/1977 | Rose et al. |
| 4,025,301 A | 5/1977 | Lang |
| 4,151,162 A | 4/1979 | Lang et al. |
| RE30,199 E | 1/1980 | Rose et al. |
| 4,545,978 A * | 10/1985 | Kalopissis et al. ............ 514/770 |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Möckli |
| 5,766,576 A | 6/1998 | Löwe et al. |
| 6,099,592 A | 8/2000 | Vidal et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 6,730,789 B1 | 5/2004 | Birault et al. |
| 7,311,736 B2 | 12/2007 | Burgaud et al. |
| 7,399,320 B2 | 7/2008 | Burgaud et al. |
| 2002/0050013 A1 | 5/2002 | Vidal et al. |
| 2003/0019051 A9 | 1/2003 | Vidal et al. |
| 2005/0028300 A1 | 2/2005 | Burgaud et al. |
| 2006/0156479 A1 | 7/2006 | Hercouet et al. |
| 2007/0172438 A1 | 7/2007 | Kruger et al. |
| 2008/0092307 A1 | 4/2008 | Burgaud et al. |
| 2009/0035335 A1 | 2/2009 | Marotta et al. |
| 2012/0251472 A1 | 10/2012 | Kurashima et al. |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 714 954 | 6/1996 |
| EP | 0 770 375 | 5/1997 |
| EP | 1 378 544 | 1/2004 |
| EP | 1 674 073 | 6/2006 |
| FR | 2 140 205 | 1/1973 |
| FR | 2 189 006 | 1/1974 |
| FR | 2 285 851 | 4/1975 |
| FR | 2 733 749 | 11/1996 |
| FR | 2 801 308 | 5/2001 |
| FR | 2 886 136 | 12/2006 |

(Continued)

OTHER PUBLICATIONS

STIC Search Report dated Jul. 25, 2013.*

(Continued)

*Primary Examiner* — Eisa Elhilo
(74) *Attorney, Agent, or Firm* — The Marbury Law Group, PLLC

(57) ABSTRACT

The present invention relates to a process for dyeing hair using at least one water-insoluble silicate, at least one compound of formula (I), in which Y represents a C1-C4 hydroxyalkyl group or a C1-C4 hydroxyalkyloxy radical, n denotes an integer ranging from 0 to 5, X, which may be identical or different, represents a C1-C4 alkyl radical or a halogen; and at least one hydroxylated aliphatic solvent comprising therein from 2 to 6 carbon atoms.

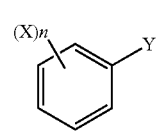

(I)

20 Claims, No Drawings

(56) References Cited

FOREIGN PATENT DOCUMENTS

| | | |
|---|---|---|
| GB | 1026978 | 4/1966 |
| GB | 1153196 | 5/1969 |
| JP | 2-19576 | 1/1990 |
| JP | 05-163124 | 6/1993 |
| JP | 2007297299 | 11/2007 |
| WO | 94/08969 | 4/1994 |
| WO | 94/08970 | 4/1994 |
| WO | 95/01772 | 1/1995 |
| WO | 95/15144 | 6/1995 |
| WO | 96/15765 | 5/1996 |
| WO | 2010/046255 | 4/2010 |
| WO | 2010/126090 | 11/2010 |

OTHER PUBLICATIONS

International Search Report for PCT/EP2011/073231.
Meylan, William M., et al., "Atom/Fragment Contribution Method for Estimating Octanol-Water Partition Coefficients," Journal of Pharmaceutical Sciences, vol. 84, No. 1, Jan. 1995, pp. 83-92.

* cited by examiner

HAIR DYEING PROCESS USING AN INSOLUBLE SILICATE, AN AROMATIC COMPOUND AND A HYDROXYLATED ALIPHATIC SOLVENT

This is a national stage application of PCT/EP2011/073231, filed internationally on Dec. 19, 2011, which claims priority to U.S. Provisional Application Nos. 61/434,076, filed on Jan. 19, 2011; 61/434,530, filed on Jan. 20, 2011 and 61/434,531, filed Jan. 20, 2011; as well as French Application Nos. FR 1060798, filed on Dec. 20, 2010; FR 1060800, filed on Dec. 20, 2011 and FR 1060803, filed on Dec. 20, 2010.

The present invention relates to a dyeing process using this composition, and to a multicompartment device containing it.

Two major methods for dyeing human keratin fibres, and in particular hair, are known.

One of these two methods is oxidation dyeing or permanent dyeing. This dyeing method uses one or more oxidation dye precursors and usually one or more oxidation bases optionally combined with one or more couplers.

In general, oxidation bases are selected from ortho- or para-phenylenediamines, ortho- or para-aminophenols and heterocyclic compounds. These oxidation bases are colourless or weakly coloured compounds which, when combined with oxidizing products, can give access to coloured species.

The shades obtained with these oxidation bases are often varied by combining them with one or more couplers, these couplers being selected especially from aromatic meta-diamines, meta-aminophenols, meta-diphenols and certain heterocyclic compounds, such as indole compounds.

The variety of molecules used as oxidation bases and couplers allows a wide range of colours to be obtained. This type of dyeing also makes it possible to obtain permanent colorations, but the use of oxidizing agents may lead to a degradation of the keratin fibres.

The second dyeing method, known as direct dyeing or semi-permanent dyeing, comprises the application of direct dyes, which are molecules that have affinity for fibres and that are colouring, even in the absence of oxidizing agent added to the compositions containing these direct dyes. Given the nature of the molecules used, they tend rather to remain on the surface of the fibre and penetrate relatively little into the fibre, when compared with the small molecules of oxidation dye precursors. These direct dyes may be natural or synthetic.

The direct dyes generally used are selected from nitrobenzene, anthraquinone, nitropyridine, azo, methine, azomethine, xanthene, acridine, azine and triarylmethane direct dyes. The chemical species used may be nonionic, anionic (acidic dyes) or cationic (basic dyes). The direct dyes may also be natural dyes.

The compositions containing one or more direct dyes are applied to the keratin fibres for a time necessary for obtaining the desired coloration, then rinsed out.

The colorations resulting therefrom are particularly chromatic colorations but are, however, only temporary or semi-permanent since their desorption from the surface and/or the core of the fibre are responsible for their lack of dyeing power and their poor fastness with respect to washing.

It is common practice to use dye compositions containing thickeners, in order to keep the dye composition on the hair during the time of reaction/penetration of the dyes into the keratin fibre and to limit the risks of running onto the face. However, the choice of these thickeners remains problematic in so far as they must not reduce the dyeing properties of the composition. In particular, the addition of thickeners must not reduce the intensity or the chromaticity of the colorations obtained on the hair. Furthermore, the addition of these thickeners sometimes leads to a decrease in the stability of the dye compositions, especially in the presence of certain organic solvents.

One of the objectives of the present invention is to obtain a composition for dyeing the hair, which is stable over time and which remains on the hair during application, while at the same time conserving the dyeing properties obtained on the hair, in particular conserving strong, chromatic and uniform colorations between the end and the root of one and the same fibre and from one fibre to another.

This objective is achieved by the present invention, one subject of which is a process for dyeing hair using a composition comprising at least one coloured or colouring species, at least one water-insoluble silicate, at least one compound of formula (I),

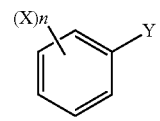

in which Y represents a C1-C4 hydroxyalkyl group or a C1-C4 hydroxyalkyloxy radical, n denotes an integer ranging from 0 to 5, X, which may be identical or different, represents a C1-C4 alkyl radical or a halogen; and at least one hydroxylated aliphatic solvent comprising therein from 2 to 6 carbon atoms.

According to one particular embodiment, one subject of the invention is a process for dyeing hair using a composition comprising a coloured or colouring species selected from natural dyes, from bases and from couplers; a water-insoluble silicate; an aromatic compound of formula (I) and an aliphatic solvent comprising therein from 2 to 6 carbon atoms.

According to one different embodiment, one subject of the invention is a process for dyeing hair using a composition comprising a coloured or colouring species selected from synthetic direct dyes; a water-insoluble silicate; an aromatic compound of formula (I) and ethanol.

Thus, the invention makes it possible to obtain thickened compositions that are stable over time without degradation of the dyeing properties and that remain in place after application to the hair.

Within the context of the invention, the expression "insoluble silicate" is understood to mean a silicate that has a solubility in water of less than 0.5%, preferably less than 0.1% by weight at 25° C.

In the description, the term "at least one" is equivalent to "one or more".

The insoluble silicates that are useful in the composition of the invention are derivatives of silica. The silicates may be natural or chemically modified (or synthetic).

The silicates correspond to optionally hydrated silica, some of the silicon atoms of which are replaced by metal cations such as $Al^{3+}$, $B^{3+}$, $Fe^{3+}$, $Ga^{3+}$, $Be^{2+}$, $Zn^{2+}$, $Mg^{2+}$, $Co^{3+}$, $Ni^{3+}$, $Na^+$, $Li^+$, $Ca^{2+}$ or $Cu^{2+}$.

More particularly, the silicates that can be used within the context of the invention are selected from:
- clays from the smectite family, such as montmorillonites, hectorites, bentonites, beidellites and saponites,
- and also clays from the vermiculite, stevensite and chlorite family.

These clays may be of natural or synthetic origin. Clays that are cosmetically compatible and acceptable with keratin materials are preferably used.

The silicate may be selected from montmorillonite, bentonite, hectorite, attapulgite and sepiolite, and mixtures thereof.

Mention may thus be made of the compounds sold by the company Laporte under the name Laponite XLG and Laponite XLS.

According to one particular embodiment, the silicate(s) are selected from laponite, montmorillonite, hectorites or bentonite, preferably laponite and montmorillonite and bentonite.

The silicate(s) may be modified with a compound selected from quaternary amines, tertiary amines, amine acetates, imidazolines, amine soaps, fatty sulphates, alkylaryl sulphonates and amine oxides, and mixtures thereof.

Suitable silicates that may be mentioned include quaternium-18 bentonites such as those sold under the names Bentone 3, Bentone 38 and Bentone 38V by the company Rheox, Tixogel VP by the company United Catalyst, Claytone 34, Claytone 40 and Claytone XL by the company Southern Clay; stearalkonium bentonites such as those sold under the names Bentone 27 by the company Rheox, Tixogel LG by the company United Catalyst and Claytone AF and Claytone APA by the company Southern Clay; quaternium-18/benzalkonium bentonites such as those sold under the names Claytone HT and Claytone PS by the company Southern Clay; quaternium-18 hectorites such as those sold under the names Bentone Gel DOA, Bentone Gel ECO5, Bentone Gel EUG, Bentone Gel IPP, Bentone Gel ISD, Bentone Gel SS71, Bentone Gel VS8 and Bentone Gel VS38 by the company Rheox, and Simagel M and Simagel SI 345 by the company Biophil. According to one particular embodiment, the silicates are not modified.

The amount of insoluble silicates may vary widely, for example between 0.1% and 20% by weight of the weight of the composition, preferably from 0.2% to 15% by weight, better still from 0.5% to 10% relative to the weight of the composition.

The coloured or colouring species are selected from oxidation bases, couplers, natural dyes and synthetic direct dyes.

The expression "natural dye" means any dye or dye precursor that has at least one natural occurrence and that is produced either by extraction (and optionally purification) from a plant matrix, or via chemical synthesis.

The natural dye(s) are for example selected from lawsone, juglone, alizarin, purpurin, carminic acid, kermesic acid, laccaic acid, purpurogallin, anthragallol, protocatechualdehyde, indigo, isatin, curcumin, spinulosin, chlorophylls, chlorophyllins, orceins, hematin, hematoxylin, brazilin, brazilein, santalin, santarubin, carthamin, flavonoids (with, for example morin, apigenidin, quercetin), anthocyans (of the apigenidin type), carotenoids, or mixtures thereof.

Use may also be made of the extracts or decoctions containing these natural dyes, and especially the extracts obtained for example from henna, pernambuco wood, logwood, sandalwood, orchil, turmeric, madder, true indigo, sorghum, cochineal, carrots, annatto, murex, brazilwood, safflower.

Preferably, the natural dye(s) are selected from lawsone, juglone, alizarin, purpurin, carminic acid, kermesic acid, laccaic acid, protocatechualdehyde, indigo, isatin, curcumin, spinulosin, apigenidin, chlorophyllin, sorghum extracts, orceins, cochineal carmine, hematin, hematoxylin, brazilin and brazilein, extracts of logwood, or of orchil or of brazilwood, and mixtures thereof.

The natural dyes or the extracts containing them represent preferably from 0.001% to 20% by weight, preferably from 0.005% to 8% by weight and better still from 0.01% to 5% by weight relative to the weight of the composition.

The expression "synthetic direct dye" means any direct dye that does not occur naturally and is obtained solely via chemical synthesis. In particular, a synthetic direct dye is not obtained by extraction (and optionally purification) from a plant matrix.

Examples of suitable direct dyes that may be mentioned include the following direct dyes: azo dyes; methine dyes; carbonyl dyes; azine dyes; nitro(hetero)aryl dyes; tri(hetero)arylmethane dyes; alone or as mixtures.

More particularly, the azo dyes comprise an —N=N— function in which the two nitrogen atoms are not simultaneously engaged in a ring. However, it is not excluded for one of the two nitrogen atoms of the sequence —N=N— to be engaged in a ring.

The dyes of the methine family are more particularly compounds comprising at least one sequence selected from >C=C< and —N=C< in which the two atoms are not simultaneously engaged in a ring. However, it is pointed out that one of the nitrogen or carbon atoms of the sequences may be engaged in a ring. More particularly, the dyes of this family are derived from compounds of true methine type (comprising one or more abovementioned sequences —C=C—); of azomethine type (comprising at least one, or more, sequences —C=N—) with, for example, azacarbocyanins and isomers thereof, diazacarbocyanins and isomers thereof, and tetraazacarbocyanins; of monoarylmethane and diarylmethane type; of indoamine (or diphenylamine) type; of indophenol type; or of indoaniline type.

As regards the dyes of the carbonyl family, examples that may be mentioned include dyes selected from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin.

As regards the dyes of the azine family, mention may be made especially of azine, xanthene, thioxanthene, fluorindine, acridine, (di)oxazine, (di)thiazine and pyronin dyes.

The nitro(hetero)aromatic dyes are more particularly nitrobenzene or nitropyridine direct dyes.

As regards the dyes of porphyrin or phthalocyanin type, it is possible to use cationic or non-cationic compounds, optionally comprising one or more metals or metal ions, for instance alkali metals, alkaline-earth metals, zinc and silicon.

Examples of particularly suitable direct dyes that may be mentioned include nitrobenzene dyes; azo direct dyes; methine direct dyes; azomethine direct dyes, with, more particularly, diazacarbocyanins and isomers thereof and tetraazacarbocyanins (tetraazapentamethines); quinone direct dyes, and in particular anthraquinone, naphthoquinone or benzoquinone dyes; azine direct dyes; xanthene direct dyes; triarylmethane direct dyes; indoamine direct dyes; indigoid direct dyes; phthalocyanine and porphyrin direct dyes; alone or as mixtures.

The direct dyes are preferably selected from nitrobenzene dyes; azo dyes; azomethine dyes, with diazacarbocyanins and isomers thereof and tetraazacarbocyanins (tetraazapentamethines); methine dyes; anthraquinone direct dyes; triarylmethane direct dyes; alone or as mixtures.

More preferably still, these direct dyes are selected from azo direct dyes; azomethine direct dyes; methine direct dyes; and anthraquinone direct dyes; alone or as a mixture.

Among the nitrobenzene direct dyes that can be used according to the invention, mention may be made in a non-limiting manner of the following compounds:

1,4-diamino-2-nitrobenzene
1-amino-2-nitro-4-β-hydroxyethylaminobenzene 1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-βγ-dihydroxypropyloxy-3-methylamino-4-nitrobenzene
1-β-hydroxyethylamino-4-β,γ-dihydroxypropyloxy-2-nitrobenzene
1-βγ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo, azomethine, and methine direct dyes that can be used according to the invention, mention may be made of the cationic dyes described in patent applications WO 95/15144, WO 95/01772 and EP 714 954; FR 2 189 006, FR 2 285 851, FR 2 140 205, EP 1 378 544 and EP 1 674 073.

Thus, mention may be made very especially of the cationic direct dyes corresponding to the following formula:

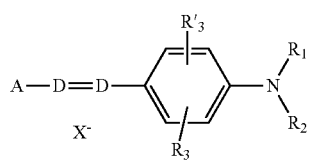

in which:
D represents a nitrogen atom or the —CH group,
$R_1$ and $R_2$, which may be identical or different, represent a hydrogen atom; a $C_1$-$C_4$ alkyl radical which may be substituted with a —CN, —OH or —NH$_2$ radical, or form, with a carbon atom of the benzene ring, an optionally oxygen-containing or nitrogen-containing heterocycle which may be substituted with one or more $C_1$-$C_4$ alkyl radicals; or a 4'-aminophenyl radical,
$R_3$ and $R'_3$, which may be identical or different, represent a hydrogen atom or a halogen atom selected from chlorine, bromine, iodine and fluorine, or a cyano, $C_1$-$C_4$ alkyl, $C_1$-$C_4$ alkoxy or acetyloxy radical,
$X^-$ represents an anion preferably selected from chloride, methyl sulphate and acetate, A represents a group selected from the following structures:

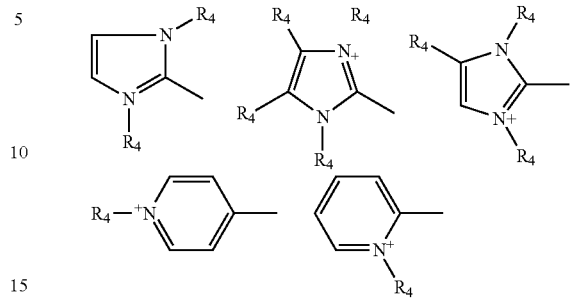

in which $R_4$ represents a $C_1$-$C_4$ alkyl radical which may be substituted with a hydroxyl radical;

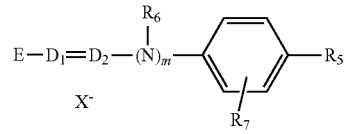

in which:
$R_5$ represents a hydrogen atom, a $C_1$-$C_4$ alkoxy radical or a halogen atom such as bromine, chlorine, iodine or fluorine,
$R_6$ represents a hydrogen atom or a $C_1$-$C_4$ alkyl radical or forms, with a carbon atom of the benzene ring, a heterocycle which optionally contains oxygen and/or is substituted with one or more $C_1$-$C_4$ alkyl groups,
$R_7$ represents a hydrogen atom or halogen atom such as bromine, chlorine, iodine or fluorine,
$D_1$ and $D_2$, which may be identical or different, represent a nitrogen atom or a —CH group,
m=0 or 1,
$X^-$ represents a cosmetically acceptable anion which is preferably selected from chloride, methyl sulphate and acetate,
E represents a group selected from the following structures:

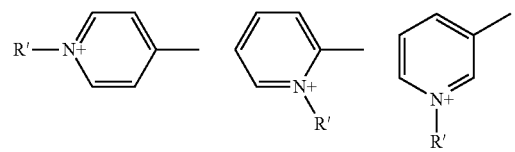

in which R' represents a $C_1$-$C_4$ alkyl radical;
when m=0 and when $D_1$ represents a nitrogen atom, E may then also denote a group of the following structure:

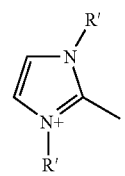

in which R' represents a $C_1$-$C_4$ alkyl radical.

Among the abovementioned compounds, use is made very particularly of the following compounds:

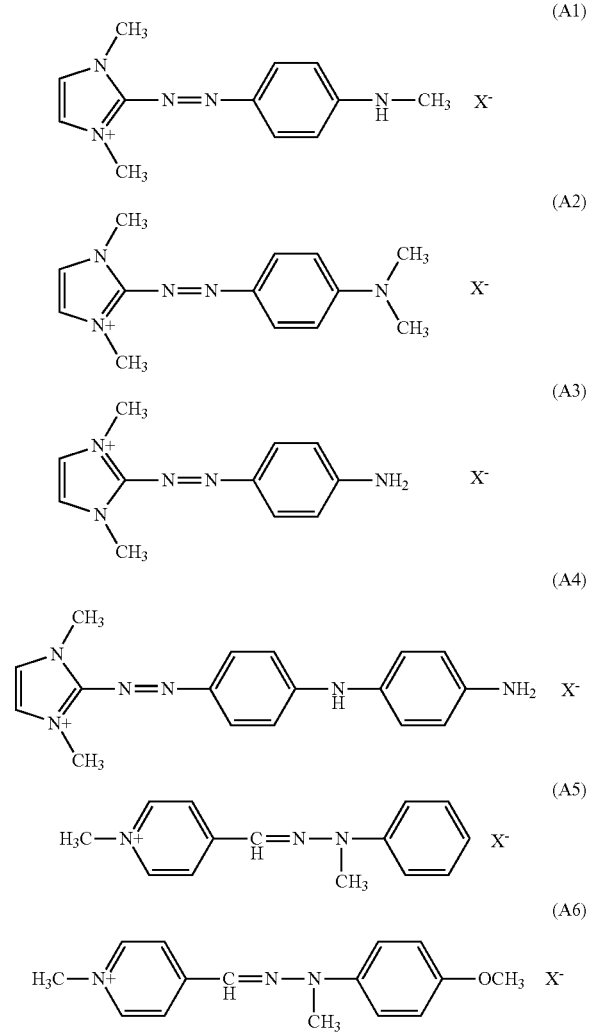

As other dyes that may be used according to the invention, mention may be made, among the azo direct dyes, of the following dyes, which are described in the Colour Index International, 3rd edition:

Disperse Red 17
Disperse Red 13
Basic Red 22
Basic Red 76
Basic Yellow 57
Basic Brown 16
Basic Brown 17
Disperse Green 9
Disperse Black 9
Solvent Black 3
Disperse Blue 148
Disperse Violet 63
Solvent Orange 7

Mention may also be made of 1-(4'-aminodiphenylazo)-2-methyl-4-bis(β-hydroxyethyl)aminobenzene (INCI name: HC Yellow 7).

Among the quinone direct dyes, mention may be made of the following dyes:

Disperse Red 15
Solvent Violet 13
Solvent Blue 14
Disperse Violet 1
Disperse Violet 4
Disperse Blue 1
Disperse Violet 8
Disperse Blue 3
Disperse Red 11
Disperse Blue 7
Disperse Blue 14
Basic Blue 22
Disperse Violet 15
Disperse Blue 377
Disperse Blue 60
Basic Blue 99 and also the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Mention may also be made of the coumarin, Disperse Yellow 82.

Among the azine dyes, mention may be made of the following compounds:

Basic Blue 17
Basic Red 2
Solvent Orange 15

Among the triarylmethane dyes that can be used according to the invention, mention may be made of the following compounds:

Basic Green 1
Basic Violet 3
Basic Violet 14
Basic Blue 7
Basic Blue 26

Among the indoamine dyes that can be used according to the invention, mention may be made of the following compounds:

2-β-hydroxyethylamino-5-[bis(β-4'-hydroxyethyl)amino]anilino-1,4-benzoquinone
2-β-hydroxyethylamino-5-(2'-methoxy-4'-amino)anilino-1,4-benzoquinone
3-N-(2'-chloro-4'-hydroxy)phenylacetylamino-6-methoxy-1,4-benzoquinone imine
3-N-(3'-chloro-4'-methylamino)phenylureido-6-methyl-1,4-benzoquinone imine
3-[4'-N-(ethyl,carbamylmethyl)amino]phenylureido-6-methyl-1,4-benzoquinone imine.

The cationic direct dyes are preferably selected from direct dyes of the following types: azo dyes, methine dyes; azomethine dyes with diazacarbocyanins and isomers thereof, and tetraazacarbocyanins (tetraazapentamethines); anthraquinone dyes; alone or as a mixture.

As regards the synthetic direct dyes with a log P of greater than or equal to 2, it is recalled that the log P value conventionally represents the partition coefficient of the dye between octanol and water. The log P may be calculated according to the method described in the article by Meylan and Howard "*Atom/fragment contribution method for estimating octanol-water partition coefficient*", J. Pharm. Sci. 84, 83-92 (1995). This value may also be calculated by means of numerous software packages available on the market, which determine the log P as a function of the structure of a molecule. An example that may be mentioned is the Epiwin software from the United States Environmental Protection Agency.

Preferably, the synthetic direct dye(s) are selected from the following dyes:

| Dye | Chemical structure | logP |
|---|---|---|
| Disperse Red 17 | 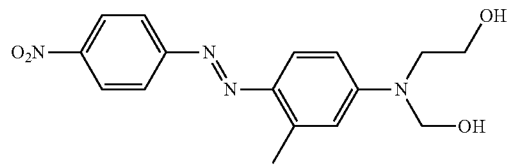 [SMILES: Cc1cc(N(CO)CCO)ccc1/N=N/c1ccc([N+](=O)[O-])cc1] | 3.69 |
| Disperse Violet 1 | 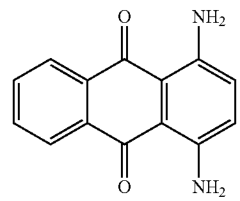 [SMILES: Nc1ccc(N)c2c1C(=O)c1ccccc1C2=O] | 3.0 |
| HC Yellow 7 | 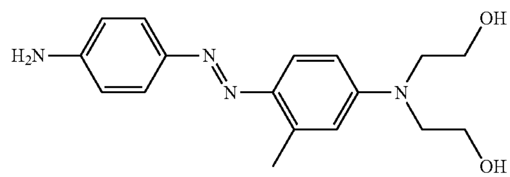 [SMILES: Cc1cc(N(CCO)CCO)ccc1/N=N/c1ccc(N)cc1] | 2.38 |
| Disperse Blue 377 | 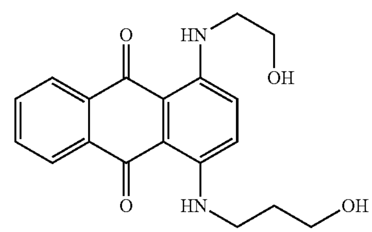 [SMILES: O=C1c2ccccc2C(=O)c2c(NCCCO)ccc(NCCO)c21] | 3.21 |
| Disperse Red 13 | 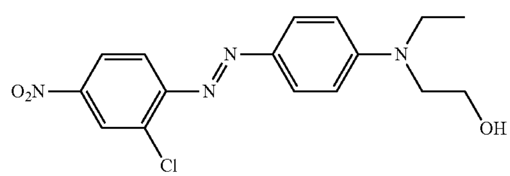 [SMILES: CCN(CCO)c1ccc(/N=N/c2ccc([N+](=O)[O-])cc2Cl)cc1] | 5.22 |
| Disperse Green 9 | 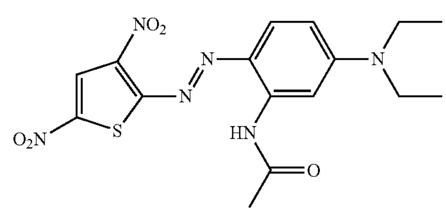 [SMILES: CCN(CC)c1ccc(/N=N/c2sc([N+](=O)[O-])cc2[N+](=O)[O-])c(NC(C)=O)c1] | 4.23 |
| Solvent Black 3 | 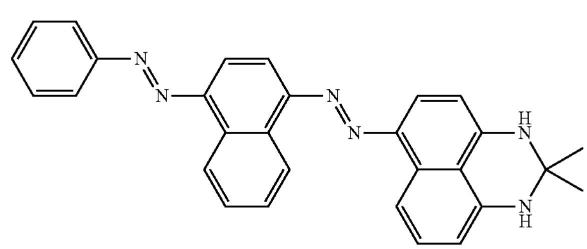 [SMILES: CC1(C)Nc2cccc3c(/N=N/c4ccc(/N=N/c5ccccc5)c5ccccc45)ccc(c23)N1] | 7.50 |

-continued

| Dye | Chemical structure | logP |
|---|---|---|
| Disperse Blue 148 | 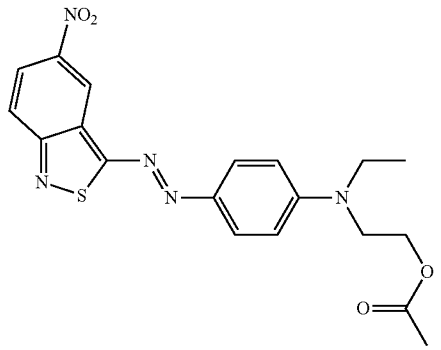 [SMILES: CCN(CCOC(C)=O)c1ccc(/N=N/c2snc3ccc([N+](=O)[O-])cc23)cc1] | 4.81 |
| Disperse Violet 63 | 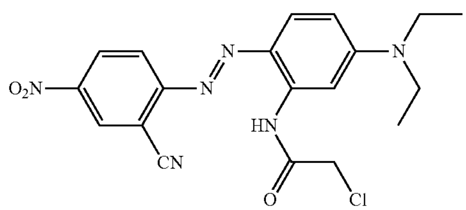 [SMILES: CCN(CC)c1ccc(/N=N/c2ccc([N+](=O)[O-])cc2C#N)c(NC(=O)CCl)c1] | 5.30 |
| Disperse Blue 60 | 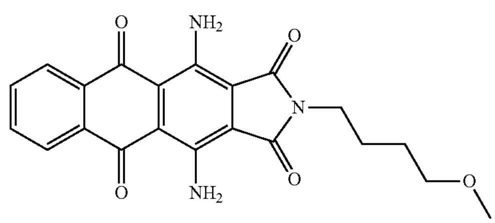 [SMILES: COCCCCn1c(=O)c2c(N)c3c(=O)c4ccccc4c(=O)c3c(N)c2c1=O] | 3.38 |
| Disperse Blue 14 | 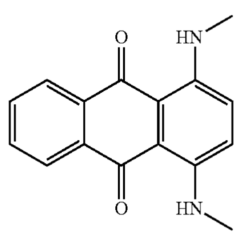 [SMILES: CNc1ccc(NC)c2c1C(=O)c1ccccc1C2=O] | 4.25 |
| Solvent Orange 15 | 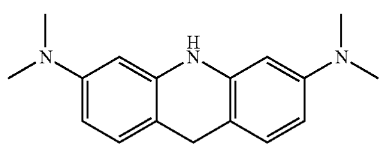 | 3.90 |
| Solvent Orange 7 | 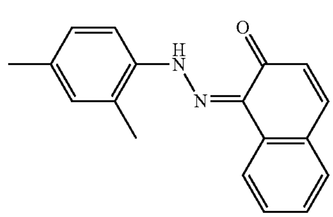 [SMILES: Cc1ccc(N/N=C2\C(=O)C=Cc3ccccc32)c(C)c1] | 4.40 |
| Solvent Blue 14 | 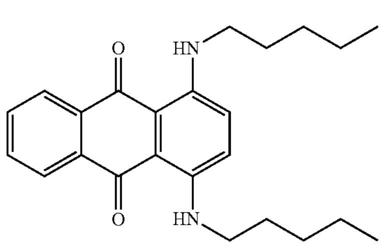 [SMILES: CCCCCNc1ccc(NCCCCC)c2c1C(=O)c1ccccc1C2=O] | 8.18 |

| Dye | Chemical structure | logP |
|---|---|---|
| Disperse Yellow 82 | (structure shown) | 3.68 |
| Dye 1 | (structure shown) | 0.62 |

More preferably still, the direct dyes of the invention are selected from cationic dyes of the following types: azo dyes; methine dyes; azomethine dyes with diazacarbocyanins and isomers thereof, and tetraazacarbocyanins (tetraazapentamethines); anthraquinone dyes; alone or as a mixture, and in particular the dyes (A1) to (A6) mentioned previously, and also nonionic dyes with a log P of greater than or equal to 2.

Among the anionic direct dyes, mention may be made in particular of those described in the COLOUR INDEX INTERNATIONAL 3rd edition under the name ACID, and in particular:

Disperse Red 17
Acid Yellow 9
Acid Black 1
Acid Yellow 36
Acid Orange 7
Acid Red 33
Acid Red 35
Acid Yellow 23
Acid Orange 24
Acid Violet 43
Acid Blue 62
Acid Blue 9
Acid Violet 49
Acid Blue 7.

According to one particular embodiment, the synthetic direct dye(s) are selected from nonionic dyes.

The synthetic direct dye(s) represent preferably from 0.0001% to 20% by weight relative to the weight of the composition, and preferably from 0.005% to 5% by weight relative to the composition.

The oxidation dyes that are useful in the composition of the invention are selected from oxidation bases and couplers.

Examples of oxidation bases that may be mentioned include para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)-tetramethylenediamine, N,N'-bis(ethyl)-N,N'-bis(4'-amino-3'-methylphenyl)-ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethyl phenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo-[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethyl-pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, and the addition salts thereof. 4,5-Diamino-1-(β-methoxyethyl)pyrazole may also be used. A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydro-pyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one. 2,3-Diamino-6,7-dihydro-1H,5H-pyrazolo[1,2-a]pyrazol-1-one and/or a salt thereof will preferably be used.

4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Among the useful couplers, mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylamino-benzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxy-ethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that can be used in the context of the invention are especially selected from the addition salts with an acid such as the hydrochlorides, hydrobromides, sulphates, citrates, succinates, tartrates, lactates, tosylates, benzenesulphonates, phosphates and acetates.

According to one embodiment, the composition comprises at least one oxidation base and optionally a coupler.

The oxidation base(s) each advantageously represent from 0.0001% to 10% by weight relative to the total weight of the composition, and preferably from 0.005% to 5% by weight relative to the total weight of the composition.

The content of coupler(s), if it is (they are) present, each advantageously represent from 0.0001% to 10% by weight relative to the total weight of the composition, and preferably from 0.005% to 5% by weight relative to the total weight of the composition.

The composition according to the invention comprises at least one compound of formula (I):

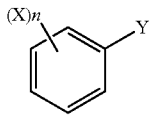

in which Y represents a C1-C4 hydroxyalkyl group or a C1-C4 hydroxyalkyloxy radical, n denotes an integer ranging from 0 to 5, X, which may be identical or different, represents a C1-C4 alkyl radical or a halogen. Preferably, n is equal to 0. According to one particular embodiment, Y represents a hydroxymethyl, hydroxyethyl or hydroxyethyloxy radical.

As examples of compounds of formula (I), mention may be made of benzyl alcohol, phenylethanol and phenoxyethanol. According to one particular embodiment, the compound of formula (I) is benzyl alcohol.

According to one particular embodiment, the amount of compounds of formula (I) ranges between 0.1% and 10% by weight of the weight of the composition, preferably from 0.1% to 5%.

The composition of the invention comprises at least one hydroxylated C2-C6 aliphatic solvent. The term "aliphatic" is understood to mean a compound that does not contain an aromatic ring. Solvents of this type may be monoalcohols or polyalcohols that are liquid at room temperature (25° C.) and at atmospheric pressure ($10^5$ Pa). These solvents are preferably not etherified. According to one particular embodiment, these solvents are selected from ethanol, glycerol, propylene glycol, dipropylene glycol and hexylene glycol. Preferably, the hydroxylated C2-C6 aliphatic solvent is ethanol and/or hexylene glycol, preferably ethanol.

According to one embodiment of the invention, the amount of hydroxylated aliphatic solvent ranges from 0.5% to 20%, preferably from 1% to 15%, better still from 2% to 10%, by weight relative to the weight of the composition.

According to one particular embodiment, the compounds of formula (I)/hydroxylated C2-C6 aliphatic solvent(s) weight ratio is less than or equal to 1, preferably between 0.1 and 1, better still from 0.1 to 0.5.

When the composition comprises natural dyes, then the composition of the invention may also comprise, associated with the dyes, metal salts such as the salts of the elements from columns 6 to 13 of the Periodic Table of the Elements, and in particular zinc, manganese, aluminium and iron salts, preferably, zinc salts. These metal salts may be introduced into the composition according to the invention or be used as a pretreatment or post-treatment. The amount of metal salts ranges from 0.001% to 20%, preferably from 0.01% to 10% and better still from 0.1% to 5% by weight of the total weight of the composition. The preferred salts are chlorides, glycinates and gluconates.

The composition according to the invention generally comprises water or a mixture of water and optionally one or more solvents other than the compounds of formula (I) and the hydroxylated C2-C6 aliphatic solvents such as polyol ethers, for instance dipropylene glycol monomethyl ether.

These additional solvents are generally present in proportions that may be between 1% and 40% by weight approximately and even more preferentially between 3% and 30% by weight approximately relative to the total weight of the dye composition.

The dye composition in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral thickeners other than the silicates described previously or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

The above adjuvants are generally present in an amount, for each of them, of between 0.01% and 20% by weight relative to the weight of the composition.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The pH of the dye composition in accordance with the invention is generally between 2 and 14 approximately. According to one particular embodiment, the pH is between 2.5 and 10 approximately. It may be adjusted to the desired value by means of acidifying or basifying agents usually used in the dyeing of keratin fibres, or alternatively using standard buffer systems.

Among the acidifying agents that may be mentioned, for example, are mineral or organic acids, for instance hydrochloric acid, orthophosphoric acid or sulphuric acid, carboxylic acids, for instance acetic acid, tartaric acid, citric acid and lactic acid, and sulphonic acids.

Among the basifying agents, examples that may be mentioned include aqueous ammonia, alkali metal carbonates, alkanolamines, such as monoethanolamine, diethanolamine and triethanolamine and derivatives thereof, sodium hydroxide, potassium hydroxide and the compounds of the following formula:

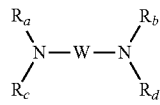

in which W is a propylene residue optionally substituted with a hydroxyl group or a $C_1$-$C_4$ alkyl radical; $R_a$, $R_b$, $R_c$, and $R_d$, which may be identical or different, represent a hydrogen atom or a $C_1$-$C_4$ alkyl or $C_1$-$C_4$ hydroxyalkyl radical.

Advantageously, the composition according to the invention has a content of basifying agent(s) ranging from 0.01% to 30% by weight and preferably from 0.1% to 20% by weight relative to the weight of said composition.

The composition according to the invention may comprise one or more oxidizing agents. Conventionally, the oxidizing agent is added to the composition at the time of use.

More particularly, the oxidizing agent(s) are selected from hydrogen peroxide, urea peroxide, alkali metal bromates or ferricyanides, peroxygenated salts, for instance alkali metal or alkaline-earth metal persulphates, perborates and percarbonates, and also peracids and precursors thereof.

The content of oxidizing agent(s) more particularly represents from 0.1% to 20% by weight and preferably from 0.5% to 10% by weight relative to the weight of the composition.

Preferably, the oxidizing agent is hydrogen peroxide in aqueous solution, the concentration of which ranges, more particularly, from 0.1% to 50% by weight, more particularly between 0.5% and 20% by weight and even more preferentially between 1% and 15% by weight relative to the weight of the composition.

The dyeing process according to the invention therefore consists in applying a composition comprising at least one water-insoluble silicate, at least one compound of formula (I), at least one hydroxylated C2-C6 aliphatic solvent and at least one natural dye to dry or wet human keratin fibres such as the hair.

According to one particular embodiment, the composition applied contains one or more oxidizing agents.

The composition is then left in place for a time usually ranging from one minute to one hour and preferably from 5 minutes to 30 minutes.

The temperature during the process is conventionally between room temperature (between 15 and 25° C.) and 80° C. and preferably between room temperature and 60° C.

After the treatment, the human keratin fibres are optionally rinsed with water, optionally washed with a shampoo and then rinsed with water, before being dried or left to dry.

EXAMPLES

Example 1

The following dye compositions are prepared from the ingredients in the proportions indicated in grams of active material:

|  | A | B | C |
|---|---|---|---|
| Laponite[a] | 3.5 g | — | — |
| Hectorite[b] | — | 3 g | — |
| Montmorillonite[c] | — | — | 4 g |
| Benzyl alcohol | 5 g | 5 g | 5 g |
| Ethanol | 15 g | 15 g | 15 g |
| Fragrance | qs | qs | qs |
| Water | qs 100 g | qs 100 g | qs 100 g |

[a]LAPONITE XLG sold by Rockwood Additives
[b]BENTONE MA sold by Elementis
[c]KUNIPIA G4 sold by KUNIMINE

|  | D |
|---|---|
| Hematin (ICHIMARU PHARCOS) | 4 g |
| Zinc phosphate | 2 g |
| Spruce powder | 0.4 g |

Locks of natural and permanent-waved hair containing 90% white hair are treated for 45 minutes at 40° C. with a mixture of 6.4 g % of the dyeing powder D and 93.6 g % of one of compositions A to C.

They are then rinsed, shampooed and dried.

Determination of the Colour

The hair coloration is evaluated in the L*a*b* system, with a MINOLTA CM2002® spectrophotometer.

In this system, L* represents the intensity; the lower the value of L*, the more intense the coloration obtained. The chromaticity is measured by the values a* and b*, a* representing the red/green axis and b* the yellow/blue axis.

Determination of the Uptake

The coloration obtained is evaluated by the measurement of ΔE, which is the variation of the colour before and after application of the dye, from the formula:

$$\Delta E = \sqrt{(L^* - L_0^*)^2 + (a^* - a_0^*)^2 + (b^* - b_0^*)^2}$$

in which L* represents the intensity and a* and b* the chromaticity of the dyed hair, and L0* represents the intensity and a0* and b0* the chromaticity of the hair before dyeing. The colour is more intense, the larger the ΔE.

Lock colorations of a strong mahogany colour are obtained. These colorations are not very selective, and are very resistant to shampooing operations and to UV rays.

| Composition | Hair | L* | a* | b* | Uptake (ΔE) |
|---|---|---|---|---|---|
| before dyeing | Natural | 61.85 | 0.68 | 12.74 | — |
|  | Perm | 58.86 | 0.21 | 11.32 | — |
| Composition A + D | Natural | 22.77 | 6.71 | 2.33 | 40.89 |
|  | Perm | 18.9 | 3.94 | 0.85 | 41.47 |
| Composition B + D | Natural | 26.62 | 9.77 | 7.46 | 36.76 |
|  | Perm | 27.24 | 13.58 | 9.36 | 34.38 |
| Composition C + D | Natural | 25.43 | 7.46 | 4.04 | 38.05 |
|  | Perm | 21.14 | 4.88 | 0.89 | 39.41 |

Example 2

The following dye compositions are prepared from the ingredients in the proportions indicated in grams of active material:

|  | A | B | C |
|---|---|---|---|
| Direct dye 1 | 0.5 g | 0.5 g | 0.5 g |
| Laponite[a] | 3.5 g | — | — |
| Hectorite[b] | — | 3 g | — |
| Montmorillonite[c] | — | — | 4 g |
| Benzyl alcohol | 5 g | 5 g | 5 g |
| Ethanol | 15 g | 15 g | 15 g |
| Fragrance | qs | qs | qs |
| pH agent | qs pH = 10 | qs pH = 10 | qs pH = 10 |
| Water | qs 100 g | qs 100 g | qs 100 g |

[a]LAPONITE XLG sold by Rockwood Additives
[b]BENTONE MA sold by Elementis
[c]KUNIPIA G4 sold by KUNIMINE

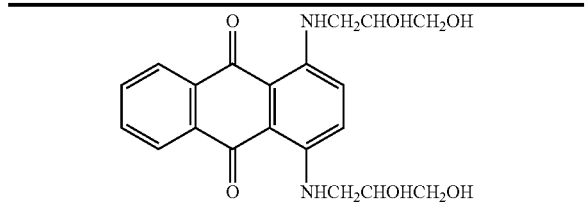

Direct dye 1

Locks of natural and permanent-waved hair containing 90% white hair are treated for 45 minutes at 40° C. with each of the compositions A to C. They are then rinsed, shampooed and dried.

Lock colorations of a strong blue colour and that are very resistant are obtained.

Example 3

The following dye composition is prepared from the ingredients in the proportions indicated in grams of active material:

|  | D |
| --- | --- |
| Disperse Red 13 dye | 0.5 g |
| Laponite[a] | 3.5 g |
| Benzyl alcohol | 5 g |
| Ethanol | 15 g |
| Fragrance | qs |
| pH agent | qs pH = 10 |
| Water | qs 100 g |

Locks of permanent-waved hair containing 90% white hair are treated for 30 minutes at 40° C. with composition D.
They are then rinsed, shampooed and dried.
Lock colorations of an intense red colour are obtained.

Example 4

The following dye compositions are prepared:

|  | 4A | 4B | 4C | 4D |
| --- | --- | --- | --- | --- |
| para-Phenylenediamine | 0.002 mol | 0.002 mol | 0.002 mol | 0.002 mol |
| 2,4-Diaminophenoxy-ethanol dihydrochloride | 0.002 mol | 0.002 mol | 0.002 mol | 0.002 mol |
| Laponite[a] | 3.5 g | — | — | — |
| Hectorite[b] | — | 3 g | — | — |
| Montmorillonite[c] | — | — | 4 g | — |
| Bentonite[d] | — | — | — | 4 g |
| Benzyl alcohol | 5 g | 5 g | 5 g | 1 g |
| Ethanol | 15 g | 15 g | 15 g | 0.5 g |
| Fragrance | qs | qs | qs | qs |
| Aqueous ammonia | qs pH = 10 | qs pH = 10 | qs pH = 10 | qs pH = 10 |
| Water | qs 100 g | qs 100 g | qs 100 g | qs 100 g |

[a]LAPONITE XLG sold by Rockwood Additives
[b]BENTONE MA sold by Elementis
[c]KUNIPIA G4 sold by KUNIMINE
[d]BENTONITE 670 NF available from BRENNTAG Each of the compositions 4A to 4D are mixed weight for weight with 20-volume aqueous hydrogen peroxide solution at pH=2.2. Each of the mixtures is then applied to locks of natural hair and permanent-waved hair containing 90% white hair. After a leave-on time of 30 minutes at room temperature, the locks are wrung out, rinsed, shampooed and dried. Lock colorations of a strong blue colour and that are very resistant are obtained.

The invention claimed is:

1. A process for dyeing hair comprising applying to the hair a composition comprising:
   at least one component chosen from natural dyes in an amount ranging from 0.005-8%, bases in an amount ranging from 0.005-10%, and couplers in an amount ranging from 0.005-10%;
   at least one water-insoluble silicate;
   at least one compound of formula (I):

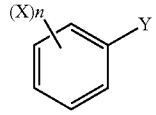

wherein Y is chosen from $C_1$-$C_4$ hydroxyalkyl groups and $C_1$-$C_4$ hydroxyalkyloxy radicals, n is an integer ranging from 0 to 5, and X, which may be identical or different, is chosen from $C_1$-$C_4$ alkyl radicals and halogen atoms; and
   at least one hydroxylated aliphatic solvent comprising from 2 to 6 carbon atoms.

2. The process according to claim 1, wherein the at least one water-insoluble silicate is chosen from montmorillonites, hectorites, bentonites, beidellites, saponites, laponite, montmorillonite and bentonite.

3. The process according to claim 1, wherein the amount of the at least one water-insoluble silicate ranges from about 0.1% to about 20% by weight relative to the total weight of the composition.

4. The process according to claim 3, wherein the amount of the at least one water-insoluble silicate ranges from about 0.5% to about 10% by weight relative to the total weight of the composition.

5. The process according to claim 1, wherein the natural dyes are chosen from at least one of lawsone, judlone, alizarin, purpurin, carminic acid, kermesic acid, laccaic acid, protocatechualdehyde, indigo, isatin, curcumin, spinulosin, apigenidin, chlorophyllin, sorghum sextracts, orceins, cochineal carmine, hematin, hematoxylin, brazilin, brazilein, extracts of logwood, extracts of orchil, and extracts of brazilwood.

6. The process according to claim 1, wherein the at least one compound of formula (I) is chosen from benzyl alcohol, phenylethanol, and phenoxyethanol.

7. The process according to claim 1, wherein the amount of the at least one compound of formula (I) ranges from about 0.1% to about 10% by weight, relative to the total weight of the composition.

8. The process according to claim 1, wherein the at least one hydroxylated aliphatic solvent comprising from 2 to 6 carbon atoms is chosen from ethanol, glycerol, propylene glycol, dipropylene glycol, hexylene glycol.

9. The process according to claim 1, wherein the weight ratio of the at least one compound of formula (I) to the at least one hydroxylated aliphatic solvent comprising from 2 to 6 carbon atoms is less than or equal to about 1.

10. The process according to claim 1, wherein the weight ratio of the at least one compound of formula (I) to the at least one hydroxylated aliphatic solvent comprising from 2 to 6 carbon atoms ranges from about 0.1 to about 0.5.

11. The process according to claim 1, wherein the composition further comprises at least one oxidizing agent.

12. A process for dyeing hair comprising applying to the hair a composition comprising:
   at least one synthetic direct dye;
   at least one water-insoluble silicate;
   at least one aromatic compound of formula (I):

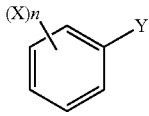

wherein Y is chosen from $C_1$-$C_4$ hydroxyalkyl groups and $C_1$-$C_4$ hydroxyalkyloxy radicals, n is an integer ranging from 0 to 5, and X, which may be identical or different, is chosen from $C_1$-$C_4$ alkyl radicals and halogen atoms; and
   ethanol.

13. The process according to claim 12, wherein the at least one water-insoluble silicate is chosen from montmorillonites, hectorites, bentonites, beidellites, saponites, preferably laponite, montmorillonite and bentonite.

14. The process according to claim 12, wherein the amount of the at least one water-insoluble silicate ranges from about 0.1% to about 20% by weight relative to the total weight of the composition.

15. The process according to claim 14, wherein the amount of the at least one water-insoluble silicate ranges from about 0.5% to about 10% by weight relative to the total weight of the composition.

16. The process according to claim 12, wherein the at least one compound of formula (I) is chosen from benzyl alcohol, phenylethanol, and phenoxyethanol.

17. The process according to claim 12, wherein the amount of the at least one compound of formula (I) ranges from about 0.1% to about 10% by weight, relative to the total weight of the composition.

18. The process according to claim 12, wherein the weight ratio of the at least one compound of formula (I) to ethanol is less than or equal to about 1.

19. The process according to claim 18, wherein the weight ratio of the at least one compound of formula (I) to ethanol ranges from about 0.1 to about 0.5.

20. The process according to claim 12, wherein the composition further comprises at least one oxidizing agent.

* * * * *